United States Patent [19]
Trapasso et al.

[11] Patent Number: 5,498,751
[45] Date of Patent: Mar. 12, 1996

[54] ORGANOTIN CATALYZED TRANSESTERIFICATION

[75] Inventors: Louis E. Trapasso, West Long Branch; Stanley J. Padegimas, Sayreville; Peter F. Epstein, Neptune City; Paul L. K. Hung, Watchung; Purnendu Mukhopadhyay, Sayreville; Philip L. Meisel, Greenbrook, all of N.J.

[73] Assignee: CPS Chemical Company, Inc., Old Bridge, N.J.

[21] Appl. No.: 116,448

[22] Filed: Sep. 3, 1993

[51] Int. Cl.$^6$ .................................................. C07C 67/02
[52] U.S. Cl. ............................................................ 560/217
[58] Field of Search .............................. 560/80, 84, 85, 560/86, 95, 96, 103, 106, 109, 112, 113, 127, 190, 193, 201, 204, 205, 217, 220, 221, 224, 225, 234

[56] References Cited

U.S. PATENT DOCUMENTS

| | | | |
|---|---|---|---|
| 3,328,439 | 6/1967 | Hamilton | 560/234 X |
| 3,642,877 | 2/1972 | Madhusudan | 560/217 |
| 3,663,569 | 5/1972 | Lew | 549/228 |
| 3,686,768 | 8/1972 | Jobert et al. | 260/465.4 |
| 3,714,234 | 1/1973 | White | 560/217 |
| 4,112,235 | 9/1978 | Schmerling | 560/217 X |
| 4,229,362 | 10/1980 | Norman | 560/224 X |
| 4,281,175 | 7/1981 | Kametani et al. | 560/217 |
| 4,301,297 | 11/1981 | Kametani et al. | 560/217 |
| 4,473,702 | 9/1984 | Seguchi | 560/80 |
| 4,547,585 | 10/1985 | Yamanaka et al. | 560/75 |
| 4,667,044 | 5/1987 | Nees et al. | 549/539 |
| 4,677,225 | 6/1987 | Nizuma et al. | 560/214 X |
| 4,745,213 | 5/1988 | Schlosser et al. | 560/217 |
| 4,845,266 | 7/1989 | Marx et al. | 560/91 |
| 4,904,814 | 2/1990 | Frei et al. | 560/96 X |
| 4,983,761 | 1/1991 | Breuer et al. | 560/217 |
| 5,286,896 | 2/1994 | Korte et al. | 560/77 |
| 5,338,882 | 8/1994 | Korte et al. | 562/483 |

FOREIGN PATENT DOCUMENTS

| | | |
|---|---|---|
| 394571 | 5/1992 | Australia . |
| 85102522 | 7/1986 | China . |
| 262589 | 7/1989 | Czechoslovakia . |
| 4317428 | 6/1994 | Germany . |
| 54-41814 | 4/1979 | Japan . |
| 58-170730 | 10/1983 | Japan . |
| 61-37337 | 2/1986 | Japan . |
| 63-115850 | 5/1988 | Japan . |
| 01265058 | 10/1989 | Japan . |
| 02067264 | 3/1990 | Japan . |
| 3041051 | 2/1991 | Japan . |
| 04095054 | 3/1992 | Japan . |

OTHER PUBLICATIONS

Aldrich, 33,568–1, 1992.
Yu et al., Huaxue Xuebao, 48(3), 287–94 (1990).
Otera et al., *Tetrahedron Lett.*, 27(21), 2383–6, (1986).
Otera et al., *J. Org. Chem.*, 54, 4013–14, (1989).
Otera et al., *J. Org. Chem.*, 56(18), 5307–11, (1991).

*Primary Examiner*—José G. Dees
*Assistant Examiner*—Samuel Barts
*Attorney, Agent, or Firm*—Lerner, David, Littenberg, Krumholz & Mentlik

[57] ABSTRACT

Esters of monocarboxylic acids are transesterified with 1,2- and 1,3-polyols by reaction in the presence of a catalytically effective amount of a dialkyltin oxide blended with an excess of dialkyltin dichloride, so that a polyol ester of the monocarboxylic acid is formed. A transesterification reaction of alcohols and polyols with methyl or ethyl mono- or polycarboxylic acid esters utilizing a dimethyltin catalyst is also disclosed, in which the alcohol or polyol carboxylic acid ester formed is essentially free of the organotin catalyst. Carboxylic acid esters produced by the described methods, as well as carboxylic acid esters that are free of organotin catalysts are also disclosed.

67 Claims, No Drawings

ORGANOTIN CATALYZED TRANSESTERIFICATION

BACKGROUND OF THE INVENTION

The present invention relates to methods for producing higher esters of carboxylic acids by an organotin catalyzed transesterification reaction between lower alkyl esters of the carboxylic acid and alcohols and polyols. In particular, the present invention relates to novel methods for forming heretofore unattainable 1,2- and 1,3-polyol esters by organotin catalyzed transesterification. In addition, the present invention relates to methods for synthesizing such polyol esters, as well as other polyol and alcohol esters, by organotin catalyzed transesterification, and recovering the resulting esters substantially free of the organotin catalyst.

Esters of unsaturated carboxylic acids and of aromatic polycarboxylic acids are of increasing commercial importance as polymerizable monomers. Materials of this nature are used to form both homopolymers and copolymers; which have commercial uses in many applications. Such applications include coatings for paper products, waste water treatment systems, optical lens coatings, floor polishes, anaerobic adhesives, pour point depressants, paper coatings, UV and EB coatings and adhesives, textile finishes, pressure sensitive adhesives, viscosity index improvers, potting compounds and sealants, photopolymers for electronics and printing plates, rubber and plastics modifiers, UV curable inks and overprint varnishes, dental and medical resins, reactive diluents for radiation curable oligomers, crosslinkers for rubber vulcanization, moisture barrier films, ion exchange resins, PVC plastisols, encapsulation and impregnation of small diameter spheres, leather finishes, binder resins for sand castings, UV curable resins for imaging systems, silane intermediates, and the like; such applications being well known to those skilled in the art.

One group of monomers of particular interest are the polyfunctional monomers; that is to say, esters of unsaturated carboxylic acids with polyfunctional alcohols. As is also well known to those skilled in the art, materials of this nature can be used as cross-linking agents to form rigid coatings which are insoluble in normally-used solvents. Of particular interest are the esters of acrylic acid (2-propenoic acid) and methacrylic acid (2-methyl-2-propenoic acid). These esters, both monofunctional and polyfunctional, have long been used as components of homopolymers and/or copolymers for the applications described above.

Another group of monomers of particular interest are the unsaturated esters of aromatic polycarboxylic acids. The polymerization products of such monomers possess excellent dielectric properties, dimensional stability, heat resistance, weatherproofness, solvent resistance and mechanical properties. Preferred polymer products also possess optimum optical properties, including transparency, refractive index and surface hardness. Such polymers are desirable for use as optical materials.

In the past, as in current industrial practice, the above monomers have been made by direct esterification, i.e., the acid catalyzed reaction of an unsaturated carboxylic acid with a mono- or polyhydric alcohol. The major exception to this procedure is the preparation of unsaturated esters containing a basic functional group, such as an amine group. In these cases, the products have traditionally been made by a transesterification procedure, using catalysts such as sodium methylate, lead oxide, tetraisopropyl titanate, and the like. (See, e.g., U.S. Pat. No. 3,642,877.) In the commercial preparation of compounds of this type, the final reaction mixture is subjected to fractional distillation under reduced pressure, in order to obtain the desired monomer in a state of high purity, free of the metallic catalyst and/or excess polymerization inhibitor, which must be present during the preparation of these compounds.

By contrast, the products of the acid-catalyzed direct esterification are purified by base-washing procedures, which will remove acid catalyst and excess unreacted carboxylic acid as well as excess polymerization inhibitors. Although, in principle, it would be possible also to purify such reaction products by fractional distillation under reduced pressure, in industrial practice this procedure is only used with materials of relatively high volatility. This is because many of these products, particularly the esters of long-chain aliphatic alcohols as well as the esters of polyhydric alcohols, have relatively high boiling points, even when high vacuum is employed. In industrial practice it is very difficult to attain pressures less than about 1 mm Hg (more usually the vacuum used varies from about 10 to 20 mm Hg); and even under these conditions, the boiling points of these esters are so high as to make them very difficult to distill. As is well known in the art, monomers of this nature will tend to polymerize at temperatures in excess of about 115°–120° C., even when inhibited with various polymerization inhibitors. Consequently, in industrial practice, it is preferred to isolate the reaction products as "bottoms" products, which are not distilled.

The acid-catalyzed direct esterification described above suffers from various disadvantages, particularly the occurrence of several side reactions. In particular, such processes may cause the formation of color bodies which may be difficult, if not impossible, to remove from the finished product. Such color bodies may render the product unsuitable for many industrial applications, in particular in areas such as paper treatment chemicals, industrial coatings and the like. Also, the acid-catalyzed side reactions will lead to the production of by-products. Such by-products, although not necessarily deleterious in themselves, act as unreactive diluents for the final product and thus reduce its efficacy. Other disadvantages include the need to use an excess of the carboxylic acid to complete the reaction. This excess carboxylic acid cannot generally be recovered and recycled; and therefore represents an extra raw material cost as well as an increased waste disposal cost.

It is, of course, possible to prepare many of these products by transesterification, but many of the same disadvantages will remain. In particular, many potential transesterification catalysts such as aluminum isopropoxide, sodium methoxide, tetraisopropyl titanate and lead oxide, also catalyze the same side reactions described above. A further disadvantage is that many of these catalysts are difficult, if not impossible, to remove from the finished product, especially on an industrial scale.

Metal-containing catalysts, such as tetraisopropyl titanate, aluminum isopropoxide or dibutyltin oxide, can be used as catalysts for transesterification reactions of monofunctional (monohydric) alcohols, as well as of polyhydric alcohols in which the hydroxyl groups are not in close proximity. However, in the case of vicinal polyols, such as ethylene glycol, 1,2-propanediol and glycerol; or in the case of polyols where the hydroxyl groups occupy 1,3-positions, such as 1,3-propanediol, trimethylolpropane, or 1,3-butanediol; metallic catalysts, such as the ones mentioned above, form, respectively, five or six-membered metal-containing cyclic compounds. These cyclic compounds are relatively unreactive and will participate only slightly, if at all, in the catalytic reaction steps needed to bring the transesterification reaction about in a reasonable length of time. It is, therefore, not feasible to use these materials as catalysts for the preparation of esters derived from the polyhydric alcohols described above.

Another metal-containing catalyst system made from dialkyltin dichlorides has recently been reported. Otera et al., *J. Org. Chem.*, 54, 4013–14 (1989) discloses that dialkyltin dichlorides form a stable, rigid, ladder structure (with four tin atoms), which functions as a template that exercises steric control during transesterification. These materials have been described as "reverse micelles" whose structure has to remain intact in order to be catalytic. Hydrocarbon solvents are preferred, because polar solvents dissociate the complex, leading to poor catalytic activity. However, predominantly non-polar reaction solvents are undesirable for the transesterification of commercially desirable carboxylic acid monomers. In addition, this reference contains no disclosure regarding how to isolate the pure product ester, a step which is essential to commercial manufacture. Furthermore, these compounds are reported to hydrolyze and form tetraorgano distannoxanes.

Otera et al., *J. Org. Chem.*, 56(18), 5307–11 (1991) disclose these compounds to be effective catalysts in the transesterification of monohydric alcohols. This is confirmed by Otera et al., *Tetrahedron Lett.*, 27(21), 2383–6 (1986), which also discloses the transesterification of diols other than 1,2- and 1,3-diols.

U.S. Pat. No. 4,473,702 discloses the synthesis of a diallyl ester of an aromatic dicarboxylic acid by transesterification of a dialkyl ester of an aromatic dicarboxylic acid with allyl alcohol. The reaction is catalyzed by a dialkyltin dichloride, dialkyltin oxide or mixtures thereof in combination with a second catalyst such as metallic magnesium, zinc, tin, lead, aluminum, nickel or zirconium, or oxides thereof. The disclosure of this patent is limited to reactions employing monohydric alcohols and the resulting ester is separated by conventional distillation and recrystallization methods, with no indication that the ester is obtained in a pure form free of the metal catalyst.

None of the foregoing publications discloses a transesterification catalyst or method that will allow for transesterification of 1,2- and 1,3-polyols, or the isolation of pure product ester. There remains a need for a catalyst system effective in the transesterification of 1,2- and 1,3-polyols. A system that would permit the isolation of the pure ester product free of the metal catalyst would be even more desirable.

SUMMARY OF THE INVENTION

It has now been found that organotin catalysts can be used in an unexpectedly different manner than described in the above-cited references to provide heretofore unattainable transesterification products in high yield and of excellent purity. The process of the present invention provides a simplified method of catalyst removal and also eliminates the need for purification by distillation. The products prepared in accordance with the methods of the present invention are substantially colorless and free of by-products and metallic catalysts.

In accordance with one embodiment of the present invention, there is provided a method for transesterifying methyl or ethyl esters of carboxylic acids with 1,2- and 1,3-polyols, including the steps of:

providing a reaction mixture including:

(1) a 1,2- or 1,3-polyol selected from aralkyl, aliphatic and cycloaliphatic polyols; and
(2) a methyl or ethyl ester of a monocarboxylic acid in stoichiometric excess of the polyol; and reacting the mixture in the presence of a catalytically effective amount of a dialkyltin oxide blended with a dialkytin dichloride, so that a polyol ester of the carboxylic acid and methanol or ethanol are formed.

This method of the present invention is particularly well suited for the transesterification of acrylate and methacrylate esters, the stoichiometric excess of which, being volatile, can be recovered and recycled. Another feature of this method is that the catalyst blend of dialkyltin dichlorides and dialkyltin oxides can be prepared in situ. Methods in accordance with this aspect of this embodiment of the present invention further include dialkyltin dichloride in the reaction mixture. The reaction step then further includes heating the reaction mixture so that the blend of dialkyltin dichloride and dialkytin oxide is formed in situ from the dialkyltin dichloride.

Reaction mixtures in accordance with this aspect of this embodiment of the present invention preferably further includes an HCl acceptor compound. Such compounds promote the in situ formation of the blend of dialkyltins.

The transesterification reaction of the present invention is reversible. Therefore, the reaction is driven closer to completion by removal of one of the reaction products from the system. For this reason, methyl or ethyl carboxylic acid starting materials are employed, so that a low boiling alcohol such as methanol or ethanol is produced, which is easier to remove from the acid esters and higher alcohol or polyol of the system. Therefore, yet another aspect of this embodiment of the present invention includes the method step of heating the reaction mixture so that the methanol or ethanol is removed from the reaction mixture, thereby permitting the reaction step to run to completion.

Preferred methods in accordance with this aspect of the invention will utilize a reaction mixture containing a solvent with which the methanol or ethanol forms a lower boiling azeotrope, and the heating step employed will heat the reaction mixture until the azeotrope is removed from the reaction mixture. The methyl or ethyl carboxylic acid ester may serve as the solvent forming the azeotrope with the methanol or ethanol. Alternatively, an auxiliary solvent may be employed, preferably an aliphatic hydrocarbon solvent with which the methanol or ethanol forms an even lower boiling azeotrope. This permits removal of the alcohol as formed without removing the methyl or ethyl carboxylic acid ester starting material, which is needed for the reaction to proceed.

In accordance with a second embodiment of the present invention, a method is provided for the preparation of a transesterification product which is catalyst-free. Not all methods in accordance with the above-described embodiment of the present invention for transesterifying lower esters of carboxylic acids with 1,2- and 1,3-polyols will produce a final product that is catalyst-free. The higher dialkyltin dichlorides such as dibutyltin dichloride will form insoluble precipitates such as dibutyltin oxide under the alkali conditions of washing transesterification mixtures. These precipitates are difficult to remove from the reaction mixture upon completion of transesterification.

The second embodiment of the present invention incorporates the unexpected discovery that dimethyltin dichloride, dimethyltin oxide and combinations thereof are completely soluble in aqueous alkali solutions, provided that the pH of these solutions is greater than 13.2. This is emphatically not the case with the corresponding dibutyltin compounds.

Therefore, one aspect of this second embodiment of the present invention employs dimethyltin dichloride and dimethyltin oxide as the preferred dialkyltin catalysts in the method of the present invention for transesterifying lower esters of carboxylic acids with 1,2- and 1,3-polyols. Not only does this method produce 1,2- and 1,3-polyol carboxylic acid esters heretofore unattainable by organotin catalyzed transesterification, the reaction product is easily isolated in a form which is catalyst-free, another objective which has been heretofore unattainable for these compounds when produced by organotin catalyzed transesterification.

Furthermore, this unexpected discovery is also applicable to the organotin catalyzed transesterification of esters of carboxylic acids with alcohols and other polyols. Until now, it likewise has not been possible to obtain the ester products of these reactions in a form free of the metal catalyst.

Therefore, in accordance with this aspect of the second embodiment of the present invention, a method is provided for transesterifying esters of carboxylic acids with alcohols and polyols including the steps of:

providing a reaction mixture including:
(1) an alcohol or polyol selected from aralkyl, aliphatic and cycloaliphatic alcohols and polyols; and
(2) a methyl or ethyl ester of a carboxylic acid selected from mono- and polycarboxylic acids in stoichiometric excess of the alcohol or polyol;

provided that the reaction mixture does not include a mixture of a polyol with a polycarboxylic acid;

reacting the mixture in the presence of a catalytically effective amount of a dimethyltin catalyst selected from dimethyltin dichloride, dimethyltin oxide and mixtures thereof, so that an alcohol or polyol ester of the carboxylic acid and methanol or ethanol are formed;

washing the reaction mixture with alkali at a pH greater than 13.2, so as to remove essentially all of the dimethyltin catalyst; and recovering the alcohol or polyol carboxylic acid ester essentially free of the dimethyltin catalyst.

When both dimethyltin compounds are present, like the polyol transesterification reaction of the present invention, a blend of dimethyltin dichloride and dimethyltin oxide can be used, or dimethyltin dichloride can be added to the reaction mixture and converted to a blend of dimethyltin dichloride and dimethyltin oxide in situ by heating the reaction mixture. Preferably, the in situ conversion can be promoted by the addition of an HCl acceptor compound to the reaction mixture.

Furthermore, completion of this transesterification reaction is similarly promoted by removal of the methanol or ethanol from the reaction mixture. This is once again accomplished by heating the reaction mixture either to boil off the methanol or ethanol by itself, or in the form of an azeotrope with the methyl or ethyl carboxylic acid ester starting material or with a non-polar hydrocarbon solvent added to the reaction mixture.

The combination of techniques described above permits the preparation of higher esters of carboxylic acids as "bottoms" products on an industrial scale. Other features of the present invention will be pointed out in the following description and claims, which disclose, by the way of example, the principles of the invention and the best modes which have been presently contemplated for carrying them out.

DETAILED DESCRIPTION OF THE PREFERRED EMBODIMENT

The transesterification reactions of the present invention can be described in terms of the following equation:

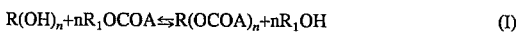

$$R(OH)_n + nR_1OCOA \rightleftharpoons R(OCOA)_n + nR_1OH \qquad (I)$$

In this equation, $R(OH)_n$ represents the alcohol or polyol whose ester is to be prepared, $R_1OH$ is the monohydric alcohol whose ester is used in the transesterification reaction; and A represents the acid from which the esters are derived. The variable n is an integer whose value can be one or greater, preferably from one to four.

The transesterification process of the present invention is operative for essentially any mono- or polycarboxylic acid ester derivative. In the above-depicted reaction scheme, A can represent an aromatic, aliphatic or cycloaliphatic mono- or polycarboxylic acid residue. The aromatic carboxylic acid residues may be derived from single ring, multiple ring and fused ring system compounds. The carboxylic acid groups may be directly substituted on an aromatic ring, or part of an alkyl group that is substituted on the ring.

In addition, the aromatic ring may be further substituted with one or more groups selected from halogen, amino, cyano, nitro, and the like, as well as alkyl, alkoxy and alkylthio groups containing from 1 to 20 carbon atoms, and the like. The alkyl groups may be saturated or unsaturated, substituted or unsubstituted and branched or unbranched. The alkyl groups, when substituted, may contain one or more of the functional groups listed above as being suitable for aromatic ring substitution. The aromatic carboxylic acid residues represented by A preferably contain between about 7 and about 20, and more preferably contain between about 8 and about 12 carbon atoms.

The aliphatic and cycloaliphatic carboxylic acid residues may be derived from saturated, monounsaturated and polyunsaturated carboxylic acids. These acids may be straight-chained or branched and may be substituted with one or more of the groups listed above as being suitable for aromatic ring substitution. The aliphatic and cycloaliphatic carboxylic acid residues represented by A preferably contain between about 2 and about 40 carbon atoms, and more preferably contain between about 3 and about 26 carbon atoms.

While the transesterification method of the present invention is functional with respect to essentially any carboxylic acid ester starting material, esters of aromatic and unsaturated aliphatic and cycloaliphatic carboxylic acids are preferred because of the utility of their transesterification reaction as polymerization monomers. The unsaturated bonds of the aliphatic and cycloaliphatic carboxylic acid esters serve as polymerization sites for the monomers. The aromatic carboxylic acid esters, on the other hand, are preferably transesterified with an unsaturated alcohol, the double bonds of which serve as polymerization sites for the monomers. While the method of the present invention can be used to synthesize higher esters of saturated aliphatic and cycloaliphatic carboxylic acids and saturated esters of aromatic carboxylic acids, these materials, unlike the preferred compounds of the present invention, can be produced by the more vigorous reaction conditions of direct esterification, and it is not essential to prepare these materials by the relatively milder conditions of transesterification.

$R_1$ in the above-depicted reaction scheme represents the alcohol portion of the carboxylic acid ester starting material. The transesterification process of the present invention results in the formation of a monohydric alcohol containing this group. While $R_1$ can represent essentially any lower alkyl group for the transesterification process of the present invention to proceed, for all practical purposes, $R_1$ is methyl or ethyl. Methyl or ethyl ester starting materials are desirable for two reasons. First, such esters function to optimize the reaction temperature and the homogeneity of the reaction mixture. Second, as is well known to those skilled in the art, the transesterification reaction of the present invention is reversible. Therefore, in order to drive the reaction to completion, it is necessary to remove one of the reaction products from the system.

Although theoretically either the new ester $R(OCOA)_n$ or the new alcohol $R_1OH$ could be removed, the transesterification process of the present invention converts the ester starting material to methanol or ethanol, respectively. These lower boiling alcohols are much simpler to remove from the reaction product mixture by direct distillation or through the formation and distillation of lower boiling azeotropes, than are higher alcohols.

Particularly preferred mono- and polycarboxylic acid ester starting materials include methyl and ethyl acrylate, methyl and ethyl methacrylate, methyl and ethyl benzoate, methyl and ethyl phthalate, methyl and ethyl trimellitate, methyl and ethyl terephthalate, methyl and ethyl isophthalate, methyl and ethyl naphthalene di- and tricarboxylates, methyl and ethyl benzene tricarboxylates, and the like. The transesterification process of the present invention will produce higher esters of these carboxylic acids.

R of the above-depicted reaction scheme represents the alcohol portion of the ester reaction to be formed in the transesterification reaction of the present invention, with $R(OH)_n$ representing the monohydric or polyhydric alcohol starting material whose ester is to be prepared. For purposes of the present invention, R will be defined as the residue of the alcohol or polyol starting material whose ester is to be prepared by the disclosed transesterification process.

In the processes of the present invention, R represents the residue of an aralkyl, aliphatic or cycloaliphatic alcohol or polyol. The hydroxyl groups of the aralkyl alcohols or polyols are alkyl-substituted. The aralkyl alcohols and polyols from which the residue R may be derived may contain a single or multiple aromatic ring or a fused ring system. Any aromatic ring may be substituted or unsubstituted. Substituted aromatic rings may contain the ring substituents described above with respect to the aromatic rings of the aromatic carboxylic acid ester starting material. Aralkyl alcohol and polyol residues in accordance with the present invention preferably contain between about 7 and about 20 carbon atoms, and more preferably contain between about 8 and about 12 carbon atoms.

The aliphatic or cycloaliphatic alcohols and polyols from which the residue R is derived may be saturated, monounsaturated or polyunsaturated. The alcohol and polyol residues may be straight-chained or branched, and substituted or unsubstituted. The substituted residues may include one or more of the groups described above as being suitable for ring substitution of the aromatic carboxylic acid starting materials of the present invention. The alcohol and polyol residues represented by R preferably contain between about 2 and about 40 carbon atoms, and even more preferably contain between about 3 and about 26 carbon atoms.

Particularly preferred alcohols and polyols for use in the transesterification process of the present invention include n- or iso- 8 to 22 carbon atom alkanols, furfuryl alcohol, tetrahydrofurfuryl alcohol, benzyl alcohol, 2-phenoxy-ethanol, cyclohexanol, allyl alcohol, methallyl alcohol, crotyl alcohol, ethylene glycol, triethylene glycol, 1,3-butanediol, trimethylolpropane, pentaerythritol, dipentaerythritol, 2,2-dimethyl-1,3-propanediol, glycerine, and the like. When reacted with methyl or ethyl acrylate or methacrylate, the transesterification process of the present invention produces higher esters of acrylic or methacrylic acid.

The transesterification process of the present invention is operative for the combination of essentially any aralkyl, aliphatic or cycloaliphatic polyol starting materials with essentially any aromatic, aliphatic or cycloaliphatic monocarboxylic acid, or with any aralkyl, aliphatic or cycloaliphatic alcohol with essentially any aromatic, aliphatic or cycloaliphatic mono- or polycarboxylic acid. The combination of polyols with polycarboxylic acids is undesirable because the reactants crosslink to form non-useful reaction products.

Again, the process of the present invention is particularly well suited for unsaturated starting materials, because unsaturated alcohols, polyols and carboxylic acids are sensitive to the more vigorous direct esterification conditions. Commercially useful monomers are typically obtained by reacting an aralkyl or saturated aliphatic or cycloaliphatic alcohol with an unsaturated aliphatic or cycloaliphatic mono- or polycarboxylic acid ester, or by reacting an unsaturated alcohol with an aromatic or saturated aliphatic or cycloaliphatic mono- or polycarboxylic acid ester. Commercially useful monomers are also obtained by reacting an aralkyl or saturated aliphatic or cycloaliphatic polyol with an unsaturated aliphatic or cycloaliphatic monocarboxylic acid ester.

Unexpectedly unique results, however, are obtained for 1,2- and 1,3-polyols with the dialkyltin catalyst system of the present invention. The catalyst system provides the high yield transesterification of such polyols without the formation of five- and six-membered metal-containing cyclic compounds that plague prior art transesterification methods. The unexpected results are obtained for the transesterification of essentially any monocarboxylic acid ester with the 1,2- and 1,3-polyols. It is also envisioned that a prepolymer could be prepared by reacting a dicarboxylic acid ester with a diol by using the art of this invention, but in this case, the molar ratio of diol to ester must be other than one to avoid forming a high viscosity product.

Unexpectedly unique results are also obtained for the transesterification of essentially any alcohol with essentially any mono- or polycarboxylic acid ester, or for the transesterification of essentially any polyol with essentially any monocarboxylic acid ester, using the dimethyltin catalyst systems of the present invention. When a dimethyltin catalyst system is employed, the transesterification product obtained after simple alkaline washing is essentially free of the organotin catalyst.

The above-depicted reaction scheme is carried out by first charging a reactor with the alcohol or polyol, followed by the methyl or ethyl ester of the mono- or polycarboxylic acid. The molar ratio of the methyl or ethyl ester of the carboxylic acid to the alcohol or polyol can be varied over a wide range, but is always greater than 1.0. Preferably, the ratio lies between about 1.2:1 and 5:1 of the methyl or ethyl carboxylic acid ester per mole of hydroxyl functionality.

A reaction temperature is selected at which the alcohol or polyol and the methyl or ethyl carboxylic acid ester are liquid. This will vary considerably because of the wide variety of carboxylic acid esters, alcohols and polyols that can be utilized with the inventive process. However, the selection of a reaction temperature at which the reactants are liquid is a matter that can be readily determined by one of ordinary skill in the art without undue experimentation. Typically, the reaction temperature will range between about 60° C. and about 140° C., and usually between about 80° C. and about 120° C.

The reaction is carried out in the presence of a dialkyltin catalyst system. Typically, the catalyst system is present at a level between about 0.01 and about 2.00 percent by weight, and more preferably at a level between about 0.05 and about 1.00 percent by weight. To obtain the transesterification of 1,2- and 1,3-polyols, a dialkyltin catalyst system consisting of dialkyltin dichloride and dialkyltin oxide is used. A stoichiometric deficiency of dialkyltin oxide is preferred, and a ratio of dialkyltin oxide to dialkyltin dichloride between about 0.5:1 and about 0.75:1 is even more preferred, in order to enhance the reaction rate.

Dialkyltin dichlorides and dialkyltin oxides having alkyl groups containing between 1 and 12 carbon atoms are suitable for use with the present invention. For the transesterification of 1,2- and 1,3-polyols, mixtures of dibutyltin oxide or dimethyltin oxide with either dibutyltin dichloride or dimethyltin dichloride are particularly effective. A mixture of dimethyltin oxide with dimethyltin dichloride is particularly preferred, because this catalyst system is readily removed from the reaction mixture to obtain a reaction product essentially free of the organotin catalyst blend.

Another feature of the method of the present invention for the transesterification of 1,2- and 1,3polyols is that the dialkyltin oxide-dialkyltin dichloride catalyst blend can be prepared in situ. The catalyst blend is formed in situ by including dialkyltin dichloride in the reaction mixture, which partially converts to the dialkyltin oxide under reaction conditions, although the transesterification reaction rate is initially slower at first until an effective quantity of the dialkyltin dichloride has converted to the dialkyltin oxide.

The in situ formation of the dialkyl dichloride-dialkyltin oxide blend can be promoted by the addition of an HCl-acceptor or alkali base to the reaction mixture, such as an alkali metal hydroxide or alkoxide, an alkaline earth metal hydroxide or oxide, an alkali or alkaline earth metal carbonate or bicarbonate, tribasic alkali phosphates, organic bases such as tertiary amines, and the like. Preferred alkali metals include lithium, sodium and potassium. Preferred alkoxides include methoxides such as sodium methylate, sodium ethoxides and sodium alkoxides of the alcohol to be transesterified. The preferred alkaline earth metal is magnesium and calcium, and the preferred tertiary amine is triethylamine. The molar ratio of the HCl-acceptor to dialkyltin dichloride can be varied over a wide range, but in general, the best results are obtained for polyhydric alcohols with a molar excess of dialkyltin dichloride.

While the nature of the alkyl groups attached to the tin atom in the dialkyltin dichlorides and oxides suitable for use in the transesterification process of the present invention can vary widely, dimethyltin dichloride and dimethyltin oxide are preferred, based upon their solubility in excess alkali and, consequently, their ready removability from the reaction mixture upon completion of the transesterification. This solubility in alkali permits the design of the commercial process in which a transesterification ester reaction product is obtained essentially free of the organotin catalysts, a property that has heretofore been unexploited. The higher dialkyltin oxides, such as dibutyltin oxide, which are either included as part of a catalyst blend, or generated in situ from dialkyltin dichlorides such as dibutyltin dichloride, form insoluble precipitates when treated with excess alkali. These precipitates are difficult to remove from the ester reaction product upon completion of the transesterification reaction.

More particularly, dimethyltin dichloride, dimethyltin oxide, and any combinations thereof, are completely soluble in aqueous alkali solutions, provided that the pH of these solutions is greater than 13.2. Accordingly, organotin compound contamination of the transesterification reaction product can be prevented by washing the reaction mixtures at pH's of 13.2 and greater. This is emphatically not the case with the corresponding dibutyltin compounds. For this reason, dimethyltin dichloride and dimethyltin oxide are the most preferred organotin catalysts for use in the processes of the present invention. The desired result can be obtained with reaction mixture pH's greater than about 13.2.

Dibutyltin compounds were listed above as among the preferred dialkyltin catalysts for the transesterification of 1,2- and 1,3-polyols. Unlike the dimethyltin catalysts, these compounds are not soluble in aqueous alkali solutions, and therefore cannot be removed from the carboxylic acid ester transesterification product by contact therewith. Dibutyltin compounds can, however, be removed from the reaction mixture at the end of the transesterification by extraction with an aqueous solution of a mineral acid or strong organic acid. Mineral acids suitable for extraction of dibutyltin compounds include hydrochloric and phosphoric acids. A suitable strong organic acid is methanesulfonic acid.

While the dimethyltin compounds are particularly preferred in the transesterification of 1,2- and 1,3-polyols so that the carboxylic acid ester reaction product is readily obtained essentially free of the residual catalyst, this concept can be extended to the transesterification of other polyols, as well as to the transesterification of alcohols. Carboxylic acid esters of these alcohols and polyols can also be readily obtained essentially free of the dimethyltin compounds by washing reaction mixtures with aqueous caustic such that the aqueous phase has pH's greater than about 13.2.

Because such mixtures of dialkyltin dichlorides and dialkyltin oxides do not form five- or six-membered rings in the presence of 1,2- and 1,3-polyols, mixtures of dimethyltin dichloride and dimethyltin oxide are suitable transesterification catalysts. Consequently, blends of dimethyltin dichloride and dimethyltin oxide, when employed, may be directly added to the reaction mixture, or formed in situ by adding dimethyltin dichloride to the reaction mixture and partially converting it to dimethyltin oxide. This procedure can be used, even with substrates in which the ring formation described above does not occur. Again, the conversion can be accelerated by adding to the reaction mixture an HCl-acceptor compound or alkali base. For the transesterification of polyols, a molar excess of dimethyltin dichloride over either dimethyltin oxide or the HCl-acceptor should be employed. For the transesterification of mono-alcohols, a stoichiometric deficiency of dimethyltin dichloride should be employed.

The foregoing is not meant to imply that dialkyltin dichlorides, dialkyltin oxides and mixtures thereof cannot be generally used to transesterify monohydric alcohols or polyols other than 1,2- and 1,3-polyols. However, the dimethyltin catalyst system of the present invention readily provides a carboxylic acid ester transesterification reaction product essentially free of the organotin catalysts.

Therefore, esters of carboxylic acids prepared in accordance with the dimethyltin catalyzed transesterification processes of the present invention will contain less than about 100 ppm of organotin compounds. The reaction product will preferably contain less than about 10 ppm organotin compounds, and ideally contain less than about 2 ppm of organotin compounds.

For transesterification reactions utilizing unsaturated carboxylic acid ester starting materials, or unsaturated monohydric or polyhydric alcohol starting materials, it is critical that polymerization of the unsaturated bonds be inhibited with one or more polymerization inhibitors. Such inhibitors are well know to those skilled in the art and include, but are not limited to, hydroquinone and its monomethyl ether, catechol, pyrocatechol, resorcinol, pyrogallol, propyl gallate, and the like.

A common feature of the above-described polymerization inhibitors is that they require the presence of oxygen to function effectively. It is, therefore, necessary to supply a stream of an oxygen-containing gas (either air or an air-nitrogen mixture) to the reaction vessel throughout the course of the transesterification reaction when such polymerization inhibitors are employed. The amount of oxygen to be used depends upon the exact product being made as well as on the size of the reactor, and can be readily determined by one of ordinary skill in the art without undue experimentation.

Another feature common to the above-listed polymerization inhibitors is that they all contain one or more phenolic hydroxyl groups. The presence of these phenolic groups enables the inhibitors to form water-soluble sodium salts when contacted with sodium hydroxide solutions. This permits the easy removal of excess phenolic inhibitors from the reaction mixture at the end of the reaction, if desired. Also, as is well understood by those of ordinary skill in the art, if desired, lower levels of inhibitors and/or different inhibitors can be added at this point. In addition, the alkali solubility of the polymerization inhibitors permits the removal from the carboxylic acid ester transesterification reaction product both the polymerization inhibitor and the residual dimethyltin transesterification catalyst by the same washing procedure.

As noted above, in order to drive the transesterification reaction of the present invention to completion, it is necessary to remove one of the reaction products from the system. Because of its lower boiling point, the ethanol or methanol generated by the transesterification is the more practical reaction product to remove. Depending upon the other reactants and reaction products, it may be possible to directly distill off the methanol or ethanol. However, in many cases, the methanol or ethanol generated will form azeotropes with the corresponding methyl or ethyl carboxylic acid ester starting material. This can be advantageous because the azeotropes generally have lower boiling points than the alcohols themselves, permitting an even simpler removal of the methanol or ethanol by distillation of the azeotrope as the alcohol is generated by the transesterification reaction. Alternatively, the methanol or ethanol may be removed by the addition of an auxiliary solvent to the reaction mixture, such as an aliphatic hydrocarbon solvent with which the alcohol forms an even lower boiling azeotrope. This permits removal of the alcohol as it is formed by the transesterification reaction without removing the methyl or ethyl carboxylic acid ester starting material which is needed for the reaction to proceed.

Thus, the reaction mixtures of the transesterification processes of the present invention may optionally include up to about 30 percent by weight, and preferably between about 5 and about 15 percent by weight of a hydrocarbon solvent among the starting materials to form a lower boiling methanol or ethanol azeotrope to assist in removing methanol or ethanol and drive the equilibrium of the transesterification reaction forward. Suitable hydrocarbon solvents include aliphatic and cycloaliphatic hydrocarbons having from about four to about eight carbon atoms. Six or seven carbon atom hydrocarbon isomer mixtures are preferred. The hydrocarbon solvent can be regenerated from the azeotrope by washing with water to extract the methanol or ethanol. The hydrocarbon solvent can then be recycled to the reaction mixture while the methanol or ethanol solution is stored for subsequent disposal or recovery.

The combination of techniques described above permits the preparation of higher esters of carboxylic acids by transesterification as "bottoms" products on an industrial scale. In addition to significantly high product yields, it is now possible to obtain the ester essentially free of the organotin reaction catalyst.

The following non-limiting examples set forth hereinbelow illustrate certain aspects of the present invention. They are not to be considered limiting as to the scope and nature of the present invention. In the examples which follow, all parts are parts by weight, and the term "molar ratio" refers to the molar ratio of alkali to dimethyltin dichloride.

EXAMPLES

EXAMPLE 1

Preparation of Cyclohexyl Methacrylate

A mixture of cyclohexanol (601 parts), methyl methacrylate (901 parts), heptane (175 parts), dimethyltin dichloride (7.25 parts), sodium methoxide (1.89 parts, molar ratio 1.06:1), 4-methoxyphenol (2.55 parts) and hydroquinone (0.85 parts) was heated together under reflux, using a 5-plate fractionating column to form and remove the heptane/methanol azeotrope generated (bp 58° C.) at varying reflux ratios. The reaction was continued until a conversion in excess of 99.0 percent was obtained. The cooled reaction mixture was washed with 10 percent aqueous sodium hydroxide to remove the tin catalyst and excess polymerization inhibitors; and finally freed from solvent by vacuum stripping.

There was formed 922 parts (92.2 percent yield, based on cyclohexanol) of cyclohexyl methacrylate, with a purity of 99 percent, containing no detectable tin as measured by atomic absorbtion spectroscopy.

EXAMPLE 2

Preparation of Ethylene Glycol Dimethacrylate

A mixture of ethylene glycol (248 parts), methyl methacrylate (1,201.4 parts), heptane (115.5 parts by weight), dimethyltin dichloride (8.8 parts), sodium methoxide (2.25 parts, molar ratio 1.04:1), 4-methoxyphenol (2.38 parts) and hydroquinone (0.79 parts) was heated together as in Example 1. The reaction was continued until a conversion in excess of 98 percent was achieved. The cooled reaction mixture was washed with ten percent aqueous sodium hydroxide to remove the tin catalyst and excess inhibitors; and finally freed from solvent by vacuum stripping.

There was formed 712 parts (90 percent yield based on ethylene glycol) of ethylene glycol dimethacrylate (EGDMA) with a total ester content of 99.1 percent and an EGDMA content of 98.0 percent, containing no detectable tin.

EXAMPLE 3

Preparation of a Mixed $C_{12}$, $C_{14}$, $C_{16}$ Methacrylate 782.8 parts of a mixture of $C_{12}$, $C_{14}$ and $C_{16}$ n-alcohols having a hydroxyl number of approximately 280–290 mg KOH/g and an average molecular weight of 195.7 daltons was mixed with 600.7 parts of methyl methacrylate, 246.5 parts of heptane, 4 parts of dimethyltin dichloride, 1.08 parts of sodium methoxide (molar ratio 1.1:1), 2.45 parts of 4-methoxy phenol and 0.83 parts of hydroquinone and heated as in Example 1 until a conversion in excess of 99 percent was obtained.

The reaction mixture was worked up as in Example 1 to yield 1,016 parts (96.3 percent yield based on starting alcohol) of product with a purity of 98.7 percent, containing no detectable tin.

EXAMPLE 4

Preparation of Isodecyl Methacrylate

In a similar manner, 634.3 parts isodecyl alcohol, 603 parts methyl methacrylate, 220.6 parts heptane, 3.1 parts dimethyltin dichloride, 1.4 parts sodium methoxide (molar ratio 1.84:1) 2.21 parts 4-methoxyphenol and 0.73 parts hydroquinone were reacted as in Example 1 to yield 185.9 parts (97.6 percent yield, based on starting alcohol) of isodecyl methacrylate having a purity of 99.0 percent and containing no detectable tin.

EXAMPLE 5

Preparation of Triethylene Glycol Dimethacrylate

In a similar manner, 450.5 parts triethylene glycol, 1,201.4 parts methyl methacrylate, 145.3 parts heptane, 6.2 parts dimethyltin dichloride, 0.77 parts sodium methoxide (molar ratio 0.50:1), 3.72 parts 4-methoxyphenol and 0.91 parts hydroquinone were reacted as in Example 1 to yield 781 parts (91 percent yield, based on triethylene glycol) of triethylene glycol dimethacrylate, having a purity of 98+percent and containing no detectable tin.

EXAMPLE 6

1, 3-Butanediol Diacrylate

A mixture of 1,3 -butanediol ( 359.7 parts ) , methyl acrylate (516.7 parts), dimethyltin dichloride (6.1 parts), sodium methoxide (1.6 parts, molar ratio 1.07:1), 4-methoxyphenol (2.7 parts) and hydroquinone (0.6 parts) was heated as in Example 1 to form and remove the methyl acrylate/methanol azeotrope (bp 62.5° C.) at varying reflux ratios. The reaction was continued until a conversion in excess of 99.0 percent was obtained. After work up as in Example 1, there was formed 1,072.8 parts (90.2 percent yield, based on 1,3-butanediol) of 1,3-butanediol diacrylate, with a purity of 99.9 percent, containing no detectable tin.

EXAMPLE 7

Preparation of Trimethylolpropane Triacrylate, Using Ethylacrylate

A mixture of trimethylolpropane (268.4 parts), ethyl acrylate (901.1 parts), dimethyltin dichloride (13.2 parts), sodium methoxide (3.5 parts, molar ratio 1:1.08), 4-methoxyphenol (3.8 parts) and hydroquinone (1.3 parts) was heated together as in Example 1 to form and remove the ethyl acrylate/ethanol azeotrope (bp 77.5° C.) at varying reflux ratios. The reaction was continued until a conversion in excess of 90.0 percent was obtained. After work up as in Example 1, there was formed 670.2 parts (99.0 percent yield, based on trimethylolpropane) of a product containing 1.3 percent monoester, 4.0 percent diester and 94.8 percent triester, containing no detectable tin.

EXAMPLE 8

Preparation of Trimethylolpropane Triacrylate, Using Methyl Acrylate

A mixture of trimethylolpropane (268.4 parts), methyl acrylate (774.8 parts), heptane (56 parts), dimethyltin dichloride (13.2 parts), sodium methoxide (1.62 parts, molar ratio 0.5:1), 4-methoxyphenol (3.8 parts) and hydroquinone (1.3 parts) was heated together as in Example 1 to form and remove the heptane/methanol azeotrope (bp 59° C.) at varying reflux ratios. The reaction was continued until a conversion in excess of 90 percent was obtained. After work up as in Example 1, there was formed 645.8 g (95.4 percent yield based on trimethylolpropane) of a product containing 0.7 percent monoester, 6.3 percent diester and 93.0 percent triester, containing no detectable tin.

EXAMPLE 9

Preparation of Isooctyl Acrylate

In a similar manner, a mixture of 520.9 parts isooctyl alcohol, 516.6 parts methyl acrylate, 183 parts heptane, 2.4 parts dimethyltin dichloride, 0.5 parts sodium hydroxide (molar ratio 1.14:1), 1.6 parts 4-methoxyphenol and 0.6 parts hydroquinone yielded, after reaction and work up as in Example 1, 715.2 parts (97 percent yield, based on isooctyl alcohol) of isooctyl acrylate with a purity of 99.9 percent, containing no detectable tin.

EXAMPLE 10

Preparation of n-Dodecylacrylate

In a similar manner, a mixture of 559 parts n-dodecyl alcohol, 387.4 parts methyl acrylate, 167 parts heptane, 1.5 parts dimethyltin dichloride, 0.4 parts sodium methoxide (molar ratio 1.08:1), 3.3 parts 4-methoxyphenol and 0.65 parts hydroquinone yielded, after work up, 672.2 parts (93.2 percent yield, based on n-dodecyl alcohol) of n-dodecyl acrylate, with a purity of 96.6 percent containing no detectable tin.

EXAMPLE 11

Preparation of Phenoxyethyl Acrylate

In a similar manner, a mixture of 414.5 parts 2-phenoxyethanol, 388 parts methyl acrylate, 141.6 parts heptane, 4.1 parts dimethyltin dichloride, 1.1 parts sodium methoxide (molar ratio 1.09:1), 1.4 parts 4-methoxyphenol and 0.5 parts hydroquinone yielded 524.8 parts (91 percent yield, based on 2-phenoxyethanol) of 2-phenoxyethyl acrylate with a purity of 98.3 percent, containing no detectable tin.

EXAMPLES 12–21

The following table lists the results obtained for other methacrylates and acrylates, using the conditions of Examples 1, 2 and 8, where applicable.

| EXAMPLE | ALCOHOL USED | ALCOHOL | METHYL METHACRYLATE | HEPTANE | DIMETHYLTIN DICHLORIDE | ALKALI | MOLAR RATIO | % YIELD | PURITY % |
|---|---|---|---|---|---|---|---|---|---|
| 12 | C16–C18 Alcohol | 758 | 451.4 | 222.4 | 3.0 | 0.8 | 1.08:1 | 95.0 | 97.2 |
| 13 | Tetrahydrofurfuryl Alcohol | 408.5 | 601.2 | 178.2 | 4:1 | 1:1 | 1.09:1 | 97.3 | 98.9 |
| 14 | Furfuryl Alcohol | 392.4 | 601.2 | 176.1 | 4:1 | 1:1 | 1.09:1 | 94.9 | 99.2 |
| 15 | Benzyl Alcohol | 432.6 | 601.2 | 182.4 | 4:1 | 1:1 | 1.09:1 | 95.7 | 98.3 |
| 16 | 2-phenoxyethanol | 414.5 | 451 | 96.2 | 4:1 | 1:1 | 1.09:1 | 97.7 | 99.1 |
| 17 | Trimethylol propane | 268.4 | 901 | — | 8.8 | 1.7 | 0.79:1 | 99 | 97 |

| EXAMPLE | ALCOHOL USED | ALCOHOL | METHYL ACRYLATE | HEPTANE | DIMETHYLTIN DICHLORIDE | ALKALI | MOLAR RATIO | % YIELD | PURITY % |
|---|---|---|---|---|---|---|---|---|---|
| 18 | Trimethylol propane | 268.4 | 774.8 | — | 8.8 | 3.2 | 1.48:1 | 91.3 | 99.1 |
| 19 | Isodecyl Alcohol | 634.3 | 518.5 | 204 | 3.1 | — | — | 93.7 | 97.8 |
| 20 | n-Dodecyl Alcohol | 559 | 387.4 | — | 1.5 | 2.67 | 1.82:1 | 96.3 | 98.4 |
| 21 | Tetrahydrofurfuryl Alcohol | 408.5 | 517 | 164.2 | 4:1 | 1:1 | 1.09:1 | 98.2 | 99.1 |

As will now be readily appreciated, the present invention provides esters of carboxylic acids via transesterification, that ordinarily could not be obtained by direct esterification. The present invention also provides 1,2- and 1,3-polyol esters that, until now, could not even be made by transesterification. Preferred embodiments of the present invention provide a simplified method for removing organotin catalyst from the carboxylic acid ester reaction product, which at the same time removes excess polymerization inhibitors. The present invention, therefore, satisfies a long-felt and heretofore unmet need for organotin catalyst-free transesterification reaction products, in general, and for 1,2- and 1,3-polyol ester reaction products in particular.

The foregoing description of the preferred embodiment should be taken as illustrating, rather than as limiting, the present invention as defined by the claims. Numerous variations and combinations of the features described above can be utilized without departing from the present invention.

What is claimed is:

1. A method for transesterifying esters of carboxylic acids with 1,2- and 1,3-polyols comprising the steps of:
   providing a reaction mixture comprising:
   (1) a 1,2- or 1,3-polyol selected from the group consisting of aralkyl, aliphatic and cycloaliphatic polyols; and
   (2) a methyl or ethyl ester of a monocarboxylic acid in stoichiometric excess of said polyol; and
   reacting said mixture at a temperature at which both said polyol and said monocarboxylic acid are liquid, and in the presence of an effective amount of a catalyst system consisting essentially of about a 1:1 ratio of a dialkyltin oxide blended with a dialkyltin dichloride, so that a polyol ester of said monocarboxylic acid and methanol or ethanol are formed.

2. The method of claim 1, wherein said dialkyltins are blended in between about a 1:2 and about a 2:1 molar ratio of said dialkyltin oxide to said dialkyltin dichloride.

3. The method of claim 2, wherein said blend of dialkyltins comprises between about a 0.5:1 and about a 0.75:1 molar ratio of said dialkyltin oxide to said dialkyltin dichloride.

4. The method of claim 1, wherein said dialkyltin dichloride and dialkyltin oxide each contain alkyl groups having from 1 to 12 carbon atoms.

5. The method of claim 4, wherein said dialkyltin dichloride comprises dimethyltin dichloride or dibutyltin dichloride and said dialkyltin oxide comprises dimethyltin oxide or dibutyltin oxide.

6. The method of claim 5, wherein said dialkyltin dichloride comprises dimethyltin dichloride and said dialkyltin oxide comprises dimethyltin oxide.

7. The method of claim 1, wherein said reacting step comprises heating said reaction mixture.

8. The method of claim 7, wherein said reaction mixture includes dialkyltin dichloride and said heating step comprises heating said dialkyltin dichloride so that said blend of dialkyltins is formed in situ.

9. The method of claim 8, wherein said reaction mixture also includes an HCl-acceptor compound so as to promote the formation of said blend of dialkyltins.

10. The method of claim 9, wherein said dialkyltin dichloride and HCl-acceptor compound are blended in about a 1:1 molar ratio.

11. The method of claim 10, wherein said reaction mixture comprises between about a 0.50:1 and about a 0.75:1 molar ratio of said HCl-acceptor compound to said dialkyltin dichloride.

12. The method of claim 8, wherein said dialkyltin dichloride comprises alkyl groups containing from 1 to about 12 carbon atoms.

13. The method of claim 12, wherein said dialkyltin dichloride comprises dibutyltin dichloride.

14. The method of claim 12, wherein said dialkyltin dichloride comprises dimethyltin dichloride.

15. The method of claim 9, wherein said HCl-acceptor compound is selected from the group consisting of alkali metal hydroxides, alkoxides, carbonates and bicarbonates, alkaline earth metal oxides, hydroxides, carbonates and bicarbonates, and organic bases.

16. The method of claim 15, wherein said alkali metal hydroxides, alkoxides, carbonates and bicarbonates are selected from the group consisting of lithium, sodium and potassium hydroxides, alkoxides, carbonates and bicarbonates.

17. The method of claim 15, wherein said alkali metal alkoxides are selected from the group consisting of alkali metal methoxides, ethoxides and alkoxides of said 1,2- and 1,3-polyols.

18. The method of claim 15, wherein said alkaline earth metal oxides, hydroxides, carbonates and bicarbonates comprise magnesium or calcium oxide, magnesium hydroxide, magnesium or calcium carbonate and magnesium bicarbonate respectively.

19. The method of claim 15, wherein said organic base comprises triethylamine.

20. The method of claim 7, wherein said heating step comprises heating said reaction mixture so that said methanol or ethanol is removed from said reaction mixture, thereby permitting the reaction step to run to completion.

21. The method of claim 20, wherein said reaction mixture comprises a solvent with which said methanol or ethanol forms an azeotrope, and said heating step comprises heating said reaction mixture until said azeotrope is removed from said reaction mixture.

22. The method of claim 21, wherein said solvent comprises said methyl or ethyl ester of said monocarboxylic acid.

23. The method of claim 21, wherein said solvent comprises an aliphatic hydrocarbon solvent, present in said reaction mixture at a level up to about 30 percent by weight.

24. The method of claim 23, wherein said hydrocarbon solvent is selected from the group consisting of aliphatic and cycloaliphatic hydrocarbons having from about 4 to about 8 carbon atoms.

25. The method of claim 1, wherein said methyl or ethyl ester comprises a methyl or ethyl ester of an unsaturated monocarboxylic acid.

26. The method of claim 25, wherein said unsaturated monocarboxylic acid ester is selected from the group consisting of acrylic acid and methacrylic acid.

27. The method of claim 1, wherein said methyl or ethyl ester of a monocarboxylic acid comprises a methyl or ethyl ester of an aromatic monocarboxylic acid.

28. The method of claim 27, wherein said aromatic carboxylic acid comprises benzoic acid.

29. The method of claim 1, wherein said 1,2 and 1,3-polyols are selected from the group consisting of ethylene glycol, triethylene glycol, 1,3-butanediol, trimethylolpropane, dipentaerythritol, 2,2-dimethyl-1,3-propanediol and glycerine.

30. The method of claim 29, wherein said methyl or ethyl ester of a monocarboxylic acid comprises a methyl or ethyl ester of acrylic acid or methacrylic acid.

31. A method for transesterifying methyl or ethyl esters of carboxylic acids with alcohols and polyols comprising the steps of:

providing a reaction mixture comprising:
  (1) an alcohol or polyol selected from the group consisting of aralkyl, aliphatic and cycloaliphatic alcohols and polyols; and
  (2) a methyl or ethyl ester of a carboxylic acid selected from the group consisting of mono- and polycarboxylic acids in stoichiometric excess of said alcohol or polyol;

provided that said reaction mixture does not include a mixture of a polyol with a polycarboxylic acid;

reacting said mixture at a temperature at which said alcohol or polyol and said carboxylic acid are liquid, and in the presence of a catalytically effective amount of a dimethyltin catalyst selected from the group consisting of dimethyltin dichloride, dimethyltin oxide and mixtures thereof, so that an alcohol or polyol ester of said carboxylic acid and methanol or ethanol are formed;

washing said reaction mixture with alkali at a pH greater than about 13.2, so as to remove essentially all of said dimethyltin catalyst; and recovering said alcohol or polyol carboxylic acid ester essentially free of said dimethyltin catalyst.

32. The method of claim 31, wherein said dimethyltin catalyst comprises a blend of dimethyltin dichloride and dimethyltin oxide.

33. The method of claim 32, wherein said reaction mixture comprises an alcohol and said blend comprises a stoichiometric excess of said dimethyltin oxide over said dimethyl dichloride.

34. The method of claim 33, wherein said dimethyltin catalyst comprises between about a 1:2 to about a 2:1 molar ratio of said dimethyltin oxide to said dimethyltin dichloride.

35. The method of claim 32, wherein said reaction mixture comprises a polyol and a monocarboxylic acid, and said blend comprises a stoichiometric excess of said dimethyltin dichloride.

36. The method of claim 31, wherein said dimethyltin catalyst consists of dimethyltin dichloride.

37. The method of claim 31, wherein said reacting step comprises heating said reaction mixture.

38. The method of claim 37, wherein said reaction mixture further includes dimethyltin dichloride and said heating step comprises heating said dimethyltin dichloride so that a dimethyltin catalyst consisting of dimethyltin dichloride and dimethyltin oxide is formed in situ, in the presence of which said alcohol or polyol and said carboxylic acid are reacted.

39. The method of claim 38, wherein said reaction mixture further includes an HCl-acceptor compound so as to promote the formation of said blend of dialkyltins.

40. The method of claim 39, wherein said reaction mixture comprises an alcohol and said HCl-acceptor compound is present in a stoichiometric excess over said dimethyltin dichloride.

41. The method of claim 40, wherein said reaction mixture comprises between about a 1:2 to a 2:1 molar ratio of said HCl-acceptor compound to said dimethyltin dichloride.

42. The method of claim 39, wherein said reaction mixture comprises a polyol and said HCl-acceptor compound is present in a stoichiometric deficiency with respect to said dimethyltin dichloride.

43. The method of claim 39, wherein said HCl-acceptor compound is selected from the group consisting of alkali metal hydroxides, alkoxides, carbonates and bicarbonates, alkaline earth metal oxides, hydroxides, carbonates and bicarbonates, and organic bases.

44. The method of claim 43, wherein said alkali metal hydroxides, alkoxides, carbonates and bicarbonates are selected from the group consisting of lithium, sodium and potassium hydroxides, alkoxides, carbonates and bicarbonates.

45. The method of claim 43, wherein said alkali metal alkoxides are selected from the group consisting of alkali metal methoxides, ethoxides and alkoxides of said alcohols and polyols.

46. The method of claim 44, wherein said alkaline earth metal oxides, hydroxides, carbonates and bicarbonates comprise magnesium or calcium oxide, magnesium or calcium, hydroxide, magnesium or calcium carbonate and magnesium bicarbonate respectively.

47. The method of claim 43, wherein said organic base comprises triethylamine.

48. The method of claim 37, wherein said heating step comprises heating said reaction mixture so that said methanol or ethanol is removed from said reaction mixture, thereby permitting the reaction step to run to completion.

49. The method of claim 48, wherein said reaction mixture comprises a solvent with which said methanol or ethanol forms an azeotrope, and said heating step comprises heating said reaction mixture until said azeotrope is removed from said reaction mixture.

50. The method of claim 49, wherein said solvent comprises said methyl or ethyl ester of said carboxylic acid.

51. The method of claim 49, wherein said solvent comprises an aliphatic hydrocarbon solvent, present in said reaction mixture at a level up to about 30 percent by weight.

52. The method of claim 51, wherein said hydrocarbon solvent is selected from the group consisting of aliphatic and cycloaliphatic hydrocarbons having from about 4 to about 8 carbon atoms.

53. The method of claim 31, wherein said reaction mixture comprises an alcohol, and said methyl or ethyl ester of said carboxylic acid comprises a polycarboxylic acid ester comprising from 2 to 4 methyl or ethyl esters, so that said alcohol ester of said polycarboxylic acid comprises from 2 to 4 ester groups.

54. The method of claim 31, wherein said methyl or ethyl ester comprises a methyl or ethyl ester of an unsaturated mono- or polycarboxylic acid.

55. The method of claim 54, wherein said unsaturated carboxylic acid is selected from the group consisting of acrylic acid and methacrylic acid.

56. The method of claim 31, wherein said methyl or ethyl ester of a carboxylic acid comprises a methyl or ethyl ester of an aromatic carboxylic acid.

57. The method of claim 56, wherein said aromatic carboxylic acid is selected from the group consisting of benzoic acid, phthalic acid, terephthalic acid isophthalic acid naphthalene di- and tricarboxylic acids, benzene tricarboxylic acid and pyromellitic acid.

58. The method of claim 31, wherein said reaction mixture comprises a polyol.

59. The method of claim 58, wherein said polyol is selected from the group consisting of ethylene glycol, 1,3-butanediol, trimethylolpropane, pentaerythritol, dipentaerythritol, 2,2-dimethyl-1,3-propanediol and glycerine.

60. The method of claim 59, wherein said methyl or ethyl ester of a carboxylic acid comprises an ester of acrylic acid or methacrylic acid.

61. The method of claim 61, wherein said alcohol or polyol is an alcohol.

62. The method of claim 61, wherein said alcohol is selected from the group consisting of n- and iso- 8 to 22 carbon atom alkanols, furfuryl alcohol, tetrahydrofurfuryl alcohol, benzyl alcohol, 2-phenoxyethanol, cyclohexanol, allyl alcohol, methallyl alcohol, crotyl alcohol and 2-phenoxy-ethanol.

63. The method of claim 62, wherein said methyl or ethyl ester of a carboxylic acid comprises an ester of acrylic acid or methacrylic acid.

64. The method of claim 62, wherein said alcohol is selected from the group consisting of allyl alcohol, methallyl alcohol and crotyl alcohol, and said methyl or ethyl ester of said carboxylic acid is selected from the group consisting of methyl and ethyl esters of benzoic acid, phthalic acid, terephthalic acid, isophthalic acid, naphthalene di- and tricarboxylic acids, benzene tricarboxylic acid and pyromellitic acid.

65. The method of claim 1, further comprising the step of washing said reaction mixture at an acid pH, so as to remove essentially all of said dialkyltin oxide and dialkyltin dichloride, so that said polyol ester of said monocarboxylic acid is recovered essentially free of said dialkyltin oxide and dialkyltin dichloride.

66. The method of claim 65, wherein said washing step comprising washing said reaction mixture with an aqueous solution of a mineral acid or strong organic acid.

67. A method for transesterifying methyl or ethyl esters of carboxylic acids with alcohols and polyols comprising the steps of:

providing a reaction mixture comprising:
(1) an alcohol or polyol selected from the group consisting of aralkyl, aliphatic and cycloaliphatic alcohols and polyols; and a methyl or ethyl ester of a carboxylic acid selected from the group consisting of mono- and polycarboxylic acids in stoichiometric excess of said alcohol or polyol;

provided that said reaction mixture does not include a mixture of a polyol with a polycarboxylic acid;

reacting said mixture at a temperature at which said alcohol or polyol and said carboxylic acid ester are liquid, and in the presence of a catalytically effective amount of a dialkyltin catalyst selected from the group consisting of dialkyltin dichloride, dialkyltin oxide and mixtures thereof, so that an alcohol or polyol ester of said carboxylic acid and methanol or ethanol are formed;

washing said reaction mixture at an acid pH, so as to remove essentially all of said dialkyltin catalysts; and recovering said alcohol or polyol carboxylic acid ester essentially free of said dialkytin catalyst.

* * * * *